US010713801B2

(12) United States Patent
Jordan et al.

(10) Patent No.: US 10,713,801 B2
(45) Date of Patent: Jul. 14, 2020

(54) IMAGE REGISTRATION OF TREATMENT PLANNING IMAGE, INTRAFRACTION 3D IMAGE, AND INTRAFRACTION 2D X-RAY IMAGE

(71) Applicant: Accuray Incorporated, Sunnyvale, CA (US)

(72) Inventors: Petr Jordan, Redwood City, CA (US); Calvin R. Maurer, Jr., San Jose, CA (US); Andriy Myronenko, San Mateo, CA (US); Jonathan Cecil Chappelow, Campbell, CA (US)

(73) Assignee: Accuray Incorporated, Sunnyvale, CA (US)

( * ) Notice: Subject to any disclaimer, the term of this patent is extended or adjusted under 35 U.S.C. 154(b) by 270 days.

(21) Appl. No.: 15/862,438

(22) Filed: Jan. 4, 2018

(65) Prior Publication Data

US 2018/0197303 A1     Jul. 12, 2018

Related U.S. Application Data

(60) Provisional application No. 62/443,581, filed on Jan. 6, 2017.

(51) Int. Cl.
*G06K 9/00*     (2006.01)
*G06T 7/33*     (2017.01)
(Continued)

(52) U.S. Cl.
CPC ............ *G06T 7/337* (2017.01); *A61B 6/032* (2013.01); *A61B 6/4258* (2013.01);
(Continued)

(58) Field of Classification Search
CPC .......... G06T 7/337; G06T 7/30; G06T 7/248; G06T 7/0012; G06T 7/0014;
(Continued)

(56) References Cited

U.S. PATENT DOCUMENTS

2008/0037843 A1    2/2008  Fu et al.
2010/0080354 A1    4/2010  Fu et al.
(Continued)

OTHER PUBLICATIONS

Ataer-Cansizoglu et al., "Towards Respiration Management in Radiation Treatment of Lung Tumors: Transferring Regions of Interest from Planning CT to Kilovoltage X-ray Images", 32nd Annual International Conference of the IEEE EMBS Buenos Aires, Argentina, Aug. 31-Sep. 4, 2010, pp. 3101-3104 (Year: 2010).*
(Continued)

*Primary Examiner* — Duy M Dang
(74) *Attorney, Agent, or Firm* — Womble Bond Dickinson (US) LLP; Daniel E. Ovanezian

(57) ABSTRACT

A method of the present disclosure includes performing, by a processing device, a first image registration between a reference image of a patient and a motion image of the patient to perform alignment between the reference image and the motion image, wherein the reference image and the motion image include a target position of the patient. The method further includes performing, by the processing device, a second image registration between the reference image and a motion x-ray image of the patient, via a first digitally reconstructed radiograph (DRR) for the reference image of the patient. The method further includes tracking at least a translational change in the target position based on the first registration and the second registration.

30 Claims, 10 Drawing Sheets

(51) Int. Cl.
*G06T 7/00* (2017.01)
*G06T 7/246* (2017.01)
*G06T 15/08* (2011.01)
*G06T 15/20* (2011.01)
*A61B 6/03* (2006.01)
*A61B 6/00* (2006.01)
*A61N 5/10* (2006.01)
*G06T 7/20* (2017.01)
*G06T 7/30* (2017.01)

(52) U.S. Cl.
CPC .......... *A61B 6/5223* (2013.01); *A61B 6/5235* (2013.01); *A61B 6/5264* (2013.01); *A61N 5/1049* (2013.01); *G06T 7/0014* (2013.01); *G06T 7/20* (2013.01); *G06T 7/248* (2017.01); *G06T 7/30* (2017.01); *G06T 15/08* (2013.01); *G06T 15/205* (2013.01); *A61N 5/103* (2013.01); *A61N 2005/1062* (2013.01); *G06T 2207/10072* (2013.01); *G06T 2207/10124* (2013.01); *G06T 2207/30004* (2013.01); *G06T 2210/41* (2013.01)

(58) Field of Classification Search
CPC . G06T 2207/10116; G06T 2207/10124; G06T 7/0028; G06T 7/20; G06K 9/20; G06K 9/00208; G06K 9/4642; A61B 6/5235; A61B 6/5229; A61B 6/5247; A61B 6/5258; A61B 6/585; A61B 6/5223; A61B 6/5264; A61B 6/032; A61B 6/4258; A61N 5/1048; A61N 5/1049
See application file for complete search history.

(56) References Cited

U.S. PATENT DOCUMENTS

2011/0210261 A1  9/2011  Maurer, Jr.
2013/0101082 A1  4/2013  Jordan et al.

OTHER PUBLICATIONS

Chappelow et al., "Multi-Attribute Combined Mutual Information (MACMI): An Image Registration Framework for Leveraging Multiple Data Channels", IEEE International Symposium on Biomedical Imaging (ISBI), 2010, pp. 376-379 (Year: 2010).*
Invitation to Pay Additional Fees and Communication Relating to the Results of the Partial International Search in PCT/US2018/012659 dated Apr. 26, 2018; 10 pgs.

* cited by examiner

IMAGE REGISTRATION OF TREATMENT PLANNING IMAGE, INTRAFRACTION 3D IMAGE, AND INTRAFRACTION 2D X-RAY IMAGE

PRIORITY CLAIM

This application claims the benefit of U.S. Provisional Application No. 62/443,581 filed on Jan. 6, 2017, the entire contents of which are hereby incorporated by reference.

TECHNICAL FIELD

The present disclosure relates to image registration of medical images.

BACKGROUND

Image guided radiation therapy (IGRT) uses images, such as treatment planning images obtained prior to radiation delivery or intra-treatment images obtain during treatment delivery, to identify the location of a treatment target (either directly or relative to a known structure within the body of a patient) within a treatment room reference frame relative to a treatment planning image reference frame. In IGRT, challenges arise when attempting to locate a target region (or a structure) within the body of the patient that moves, either just prior to, or during the course of radiation treatment, from its location within the body when the treatment planning image was acquired. Image registration provides the ability to locate a target region within the body by comparing the image content between two or more images.

BRIEF DESCRIPTION OF THE DRAWINGS

The present disclosure will be understood more fully from the detailed description given below and from the accompanying drawings of various implementations of the disclosure.

DETAILED DESCRIPTION

Described herein are embodiments of methods and apparatus for image registration of medical images such as a treatment planning image (e.g., a reference image), an intrafraction image (e.g., a motion image), and an intrafraction x-ray image (e.g., a motion x-ray image). In one embodiment, a two-stage image registration method is described that consecutively registers images of three imaging modalities: a treatment planning image, an intrafraction image, and an intrafraction x-ray image.

Figure 1A:
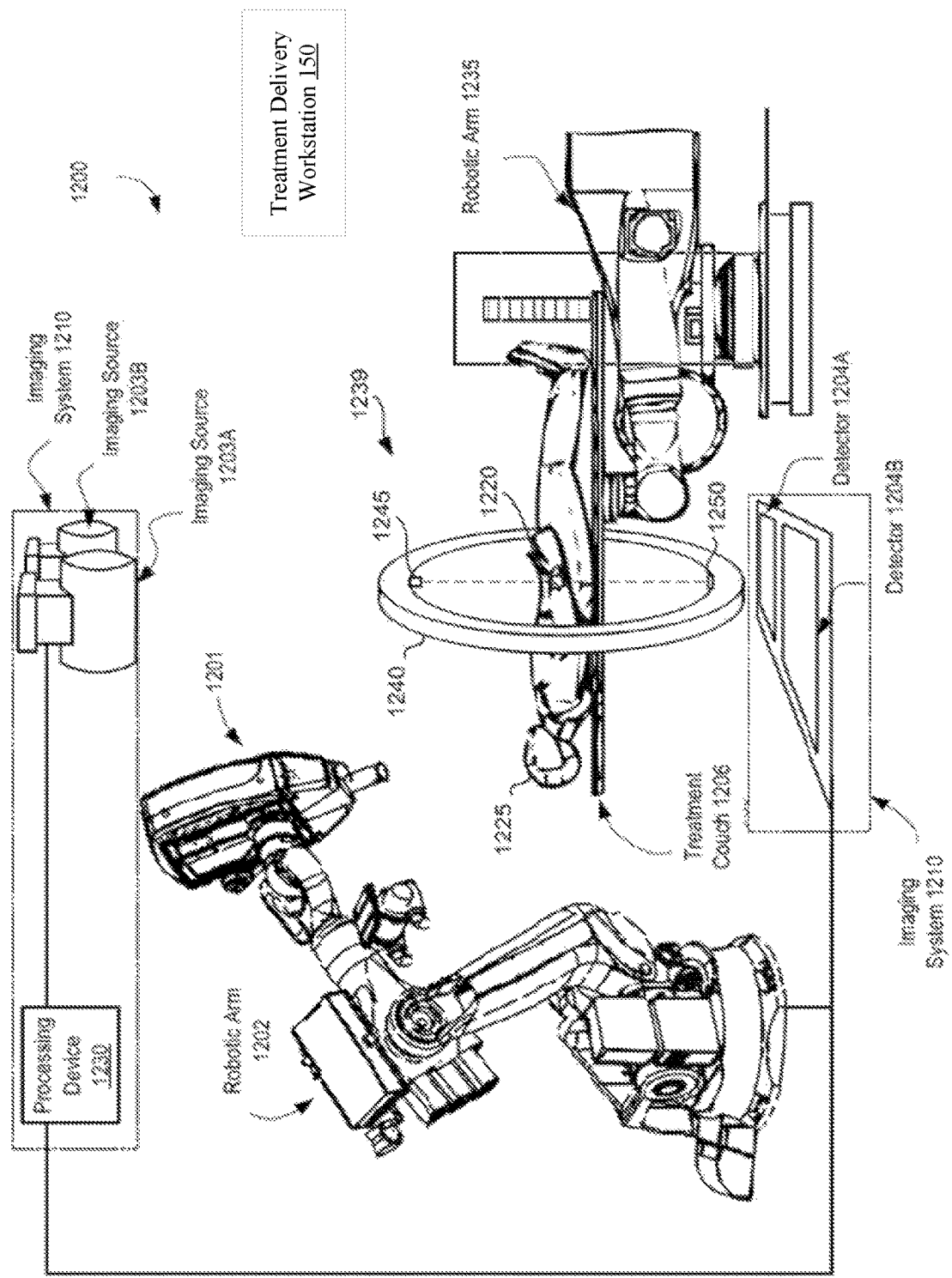
FIG. 1A illustrates a radiation treatment system that may be used in accordance with embodiments described herein.

The use of a volumetric imaging system (e.g., the medPhoton ImagingRing System (IRS)) with a radiation treatment delivery system (e.g., the CyberKnife® radiation treatment system) as shown in FIG. 1A enables new image registration and image tracking opportunities. Worth noting, the term "tracking" used herein may refer to both tracking a treatment target in the treatment planning stages (e.g., determining a location of the treatment target) as well as tracking the treatment target during treatment (e.g., actively updating a location of the treatment target). While the volumetric imaging system (e.g., 1239) may provide superior anatomical information and robust patient alignment, the stereoscopic x-ray imaging system (e.g., 1210) enables frequent intrafraction imaging and tracking. In an alternative embodiment, a radiation therapy device with an integrated in-room diagnostic computer tomography (CT) may be used. With an in-room diagnostic CT, the patient is physically moved (e.g., using a robotic couch) between an in-room diagnostic scanner and the radiation treatment delivery system.

As used herein, "registration" (also referred to herein as "image registration") of medical images refers to the determination of a mathematical relationship between corresponding anatomical or other features (e.g. fiducials) appearing in those medical images. In one embodiment, patients may be imaged multiple times, either with a single modality, or with different modalities. On step when interpreting and comparing image sets is the establishment of correspondence between different points in the multiple images. Image registration is the process of computing a mapping or transformation between coordinates in one image space and those in another. This transformation results in the same anatomical points in different image sets being mapped to each other, and can be used to fuse image sets in order to use the combined imaging information for diagnosis and treatment.

Image registration and fusion may be useful in a variety of contexts, including when combining complementary structural information such as soft tissue from MR with bone from CT. Image fusion is also very useful for interpreting functional imaging. When functional PET or fMR images are fused with high-resolution anatomical images, the functional properties can be linked to the anatomical structures in which they occur.

Registration can include, but is not limited to, the determination of one or more spatial, alignment or intrafraction transformations that, when applied to one or both of the medical images, would cause an overlay of the corresponding anatomical features. The spatial or alignment or intrafraction transformations can include rigid-body transformations and/or deformable transformations and can, if the medical images are from different coordinate systems or reference frames, account for differences in those coordinate systems or reference frames.

Image registration in general may involve computation of similarity values or, equivalently, difference values (e.g., cross correlation, entropy, mutual information, gradient correlation, pattern intensity, gradient difference, image intensity gradients) that are evaluated to determine a spatial transformation between a target's location in a planning room image and a target's location in a treatment room image. Other methods of image registration may be utilized.

For cases in which the medical images are not acquired using the same imaging system and are not acquired at the same time, the registration process can include, but is not limited to, the determination of a first transformation that accounts for differences between the imaging modalities, imaging geometries, and/or frames of reference of the different imaging systems, together with the determination of a second transformation that accounts for underlying anatomical differences in the body part that may have taken place (e.g., positioning differences, overall movement, relative movement between different structures within the body part, overall deformations, localized deformations within the body part, and so forth) between acquisition times.

Various image registration methods may be utilized with the embodiments described herein. In one example, point-based registration may be used. Points are simple geometrical features that can be used for medical image registration. Point-based registration involves determining the 3-D coordinates of corresponding points in the two images and computing the transformation that best aligns these points.

In another embodiment, surface-based registration may be used. The 3-D boundary or surface of an anatomical object or structure is a geometrical feature that can be used for medical image registration. Surface-based image registration methods may involve determining corresponding surfaces in the two images and computing the transformation that best aligns these surfaces. Whereas point-based registration involves aligning a generally small number of corresponding fiducial points, surface-based registration involves aligning a generally much larger number of points for which no point correspondence information is available.

In another embodiment, intensity-based registration may be used. Intensity-based registration may involve calculating a transformation between two images using a measure of alignment based only on the values of the pixels or voxels in the images. In other embodiments, other methods of image registration may be used.

The term alignment transformation (e.g., volumetric alignment) refers herein to a transformation between a first coordinate system (for example and not by way of limitation a planning image coordinate system of a patient) and a second coordinate system (a treatment room coordinate system) whereby the alignment transformation determines the location of a target in the second coordinate system relative to the first coordinate system, for example and not by way of limitation at the time of patient setup prior to commencement of the treatment fraction.

The term intrafraction transformation refers herein to a transformation between the first coordinate system and the second coordinate system whereby the intrafraction transformation determines the location of the target in the first coordinate system relative to the second coordinate system following commencement of the procedure, for example and not by way of limitation during the treatment fraction.

The term target may refer to one or more fiducials near (within some defined proximity to) a treatment area (e.g., a tumor). In another embodiment a target may be a bony structure. In yet another embodiment a target may refer to soft tissue of a patient. A target may be any defined structure or area capable of being identified and tracked, as described herein.

There is a need to improve on image registration methods to increase the accuracy and computational efficiency in locating a target in one or more images, and thereby more accurately and efficiently determine the spatial transformation between the target's location in a treatment room reference frame relative to a treatment planning image reference frame.

FIG. 1A illustrates a radiation treatment system 1200 that may be used in accordance with embodiments described herein. As shown, FIG. 1A illustrates a configuration of a radiation treatment system 1200. In the illustrated embodiments, the radiation treatment system 1200 includes a linear accelerator (LINAC) 1201 that acts as a radiation treatment source. In one embodiment, the LINAC 1201 is mounted on the end of a robotic arm 1235 having multiple (e.g., 5 or more) degrees of freedom in order to position the LINAC 1201 to irradiate a pathological anatomy (e.g., target 120) with beams delivered from many angles, in many planes, in an operating volume around a patient. Treatment may involve beam paths with a single isocenter, multiple isocenters, or with a non-isocentric approach. Alternatively, other types of image guided radiation treatment (IGRT) systems may be used. In one alternative embodiment, the LINAC 1201 may be mounted on a gantry based system as described below.

LINAC 1201 may be positioned at multiple different nodes (predefined positions at which the LINAC 1201 is stopped and radiation may be delivered) during treatment by moving the robotic arm 1235. At the nodes, the LINAC 1201 can deliver one or more radiation treatment beams to a target. The nodes may be arranged in an approximately spherical distribution about a patient. The particular number of nodes and the number of treatment beams applied at each node may vary as a function of the location and type of pathological anatomy to be treated.

The radiation treatment system 1200 includes an imaging system 1210 having a processing device 1230 connected with x-ray sources 1203A and 1203B (i.e., imaging sources) and fixed x-ray detectors 1204A and 1204B. Alternatively, the x-ray sources 103A, 1203B and/or x-ray detectors 1204A, 1204B may be mobile, in which case they may be repositioned to maintain alignment with the target 120, or alternatively to image the target from different orientations or to acquire many x-ray images and reconstruct a three-dimensional (3D) cone-beam CT. In one embodiment, the x-ray sources are not point sources, but rather x-ray source arrays, as would be appreciated by the skilled artisan. In one embodiment, LINAC 1201 serves as an imaging source, where the LINAC power level is reduced to acceptable levels for imaging.

Imaging system 1210 may perform computed tomography (CT) such as cone beam CT or helical megavoltage computed tomography (MVCT), and images generated by imaging system 1210 may be two-dimensional (2D) or three-dimensional (3D). The two x-ray sources 1203A and 1203B may be mounted in fixed positions on the ceiling of an operating room and may be aligned to project x-ray imaging beams from two different angular positions (e.g., separated by 90 degrees) to intersect at a machine isocenter (referred to herein as a treatment center, which provides a reference point for positioning the patient on a treatment couch 1206 during treatment) and to illuminate imaging planes of respective detectors 1204A and 1204B after passing through the patient. In one embodiment, imaging system 1210 provides stereoscopic imaging of a target and the surrounding volume of interest (VOI). In other embodiments, imaging system 1210 may include more or less than two x-ray sources and more or less than two detectors, and any of the detectors may be movable rather than fixed. In yet other embodiments, the positions of the x-ray sources and the detectors may be interchanged. Detectors 1204A and 1204B may be fabricated from a scintillating material that converts the x-rays to visible light (e.g., amorphous silicon), and an array of CMOS (complementary metal oxide silicon) or CCD (charge-coupled device) imaging cells that convert the light to a digital image that can be compared with a reference image during an image registration process that transforms a coordinate system of the digital image to a coordinate system of the reference image, as is well known to the skilled artisan. The reference image may be, for example, a digitally reconstructed radiograph (DRR), which is a virtual x-ray image that is generated from a 3D CT image based on simulating the x-ray image formation process by casting rays through the CT image.

IGRT delivery system 1200 also includes a secondary imaging system 1239. Imaging system 1239 is a Cone Beam Computed Tomography (CBCT) imaging system, for example, the medPhoton ImagingRing System. Alternatively, other types of volumetric imaging systems may be used. The secondary imaging system 1239 includes a rotatable gantry 1240 (e.g., a ring) attached to anarm and rail system (not shown) that move the rotatable gantry 1240 along one or more axes (e.g., along an axis that extends from a head to a foot of the treatment couch 1206. An imaging source 1245 and a detector 1250 are mounted to the rotatable gantry 1240. The rotatable gantry 1240 may rotate 360 degrees about the axis that extends from the head to the foot of the treatment couch. Accordingly, the imaging source 1245 and detector 1250 may be positioned at numerous different angles. In one embodiment, the imaging source 1245 is an x-ray source and the detector 1250 is an x-ray detector. In one embodiment, the secondary imaging system 1239 includes two rings that are separately rotatable. The imaging source 1245 may be mounted to a first ring and the detector 1250 may be mounted to a second ring. In one embodiment, the rotatable gantry 1240 rests at a foot of the treatment couch during radiation treatment delivery to avoid collisions with the robotic arm 1202.

As shown in FIG. 1A, the image-guided radiation treatment system 1200 may further be associated with a treatment delivery workstation 150. The treatment delivery workstation may be remotely located from the radiation treatment system 1200 in a different room that the treatment room in which the radiation treatment system 1200 and patient are located. The treatment delivery workstation 150 may include a processing device (which may be processing device 1230 or another processing device) and memory that modify a treatment delivery to the patient 1225 based on a detection of a target motion that is based on one or more image registrations, as described herein.

In some embodiments, a gantry system with a helical delivery may be used to rotate the imaging system 1210. For example, the gantry system may be used to acquire two, three, or more images (e.g., x-ray images) at different angles. The radiation treatment delivery system may also include a rotational imaging system 109 that is positioned around the patient.

In one implementation, the system 1200 is coupled to a frameless robotic radiosurgery system (e.g., CyberKnife® treatment delivery system). In another implementation, the system 1200 is coupled to a gantry-based LINAC treatment system where, for example, LINAC 1201 is coupled to a gantry of a gantry based system. Alternatively, system 1200 may be used with other types of radiation treatment systems, for example, a helical delivery system as discussed below.

Figure 1B:
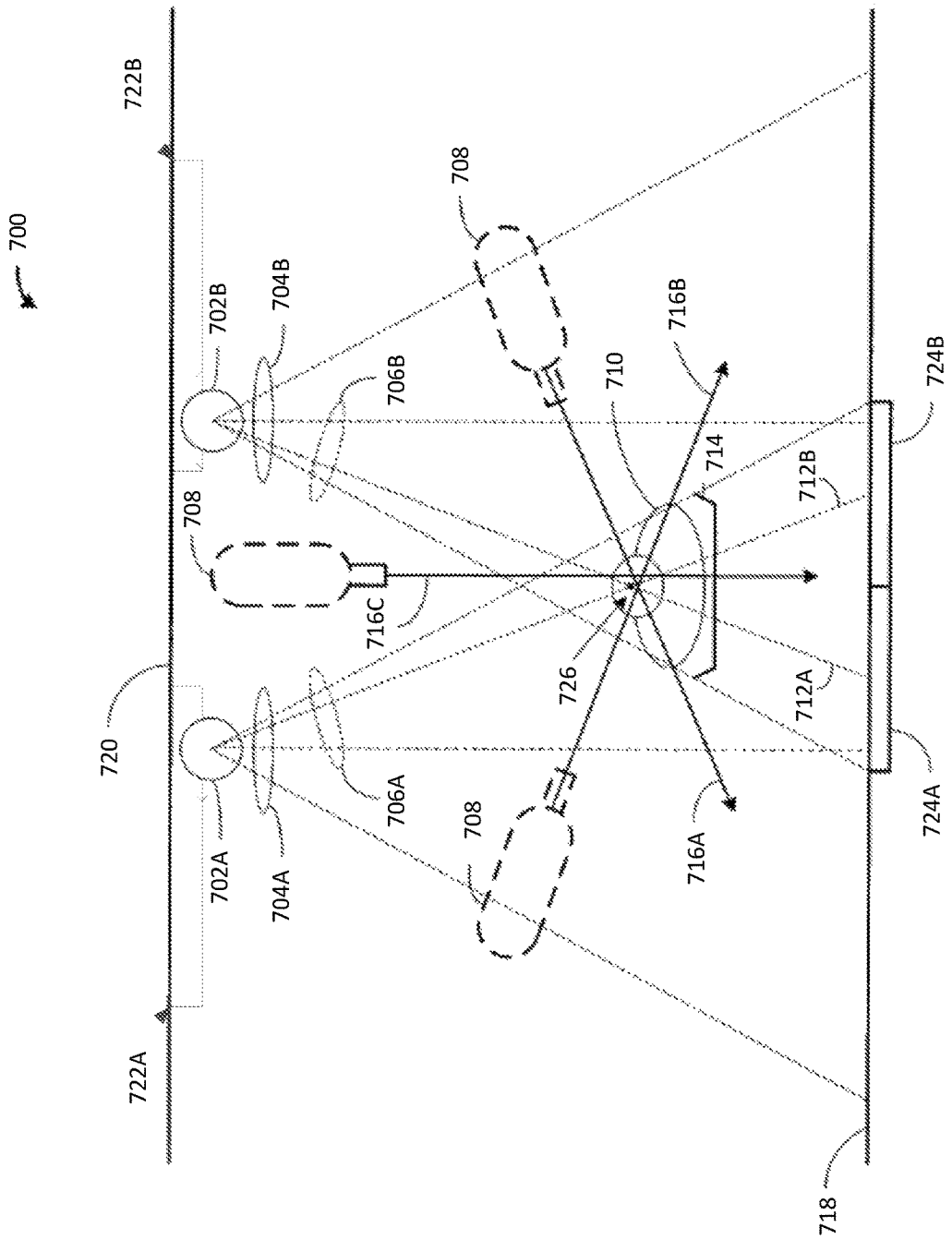
FIG. 1B is a cross-section of the radiation treatment system in accordance with embodiments described herein.

FIG. 1B illustrates the configuration of an image-guided radiation treatment (IGRT) system 700. In general, the IGRT system 700 may correspond to the radiation treatment system 1200 of FIG. 1A.

As shown in FIG. 1B, the IGRT system 700 may include to kilovoltage (kV) imaging sources 702A and 702B that may be mounted on tracks 722A and 722B on the ceiling 720 of an operating room and may be aligned to project imaging x-ray beams 704A and 704B from two different positions such that a ray 712A of beam 704A intersects with a ray 712B of beam 704B at an imaging center 726 (i.e., isocenter), which provides a reference point for positioning the LINAC 708 to generate treatment beams 716A, 716B and 716C and the patient 710 on treatment couch 714 during treatment. After passing through the patient 710, imaging x-ray beams 704A and 704B may illuminate respective imaging surfaces of x-ray detectors 724A and 724B, which may be mounted at or near the floor 718 of the operating room and substantially parallel to each other (e.g., within 5 degrees). The kV imaging sources 702A and 702B may be substantially coplanar such that the imaging surfaces of kV imaging sources 702A and 702B form a single imaging plane. In one embodiment, kV imaging sources 702A and 702B may be replaced with a single kV imaging source. Once an x-ray image of the patient 714 has been generated, the LINAC 708 may rotate to generate a treatment beam 716 from a different angle. While the LINAC 708 rotates to the different angle, the kV imaging sources 702A and 702B may move along tracks 722A and 722B to generate x-ray images of the patient 710 from a new angle.

Figure 2:
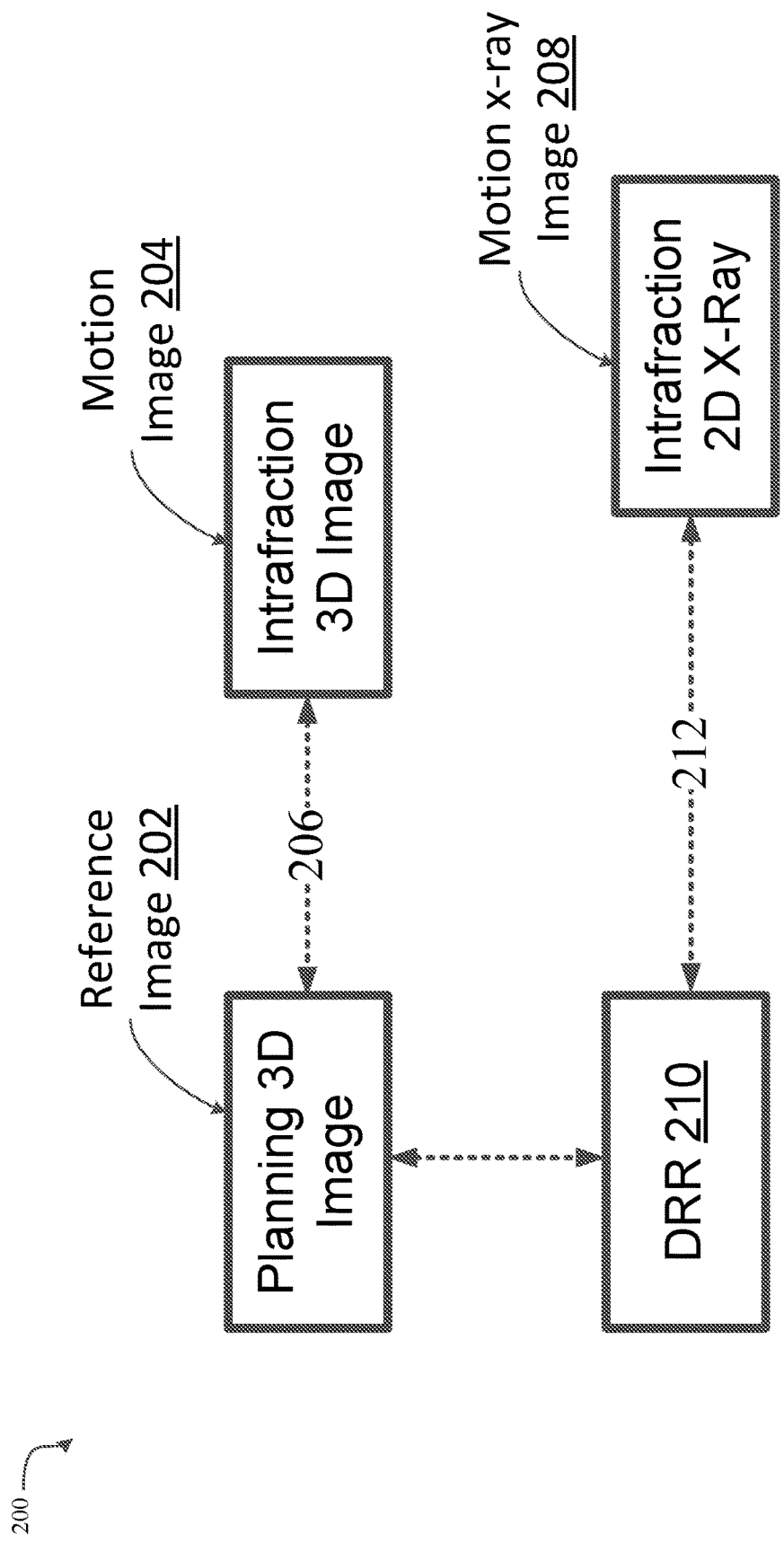
FIG. 2 illustrates an image registration pipeline in accordance with a first embodiment described herein.

FIG. 2 illustrates an image registration pipeline 200 in accordance with a first embodiment described herein. In the first stage, a reference image 202 (e.g., a treatment planning image, such as an MRI, PET, CT or ultrasound) is registered to a motion image 204 (e.g., an intrafraction 3D image such as a kV CBCT, MV CBCT or MVCT) to achieve global patient alignment between the position of the patient during the treatment plan and daily patient position during treatment delivery. In one embodiment, the registration 206 is a 3D to 3D image registration employing either 3D rigid (e.g., translation only), six-dimensional (6D) rigid (e.g., translation and rotation), or nonrigid transformation. It should be noted that these are non-limiting examples of various types of transformations that may be used, and that in alternative embodiments other transformations may be used. For example a four-dimensional (4D) transformation that is 3D rigid (translation) plus a rotation angle (roll).

In a second stage, the reference image 202 may be registered to a motion x-ray image 208 (e.g., an intrafraction 2D X-Ray image), using a DRR 210 generated from the reference image 202 to perform 2D/3D image registration 212. Consequently, the intrafraction X-Ray image becomes implicitly registered to the intrafraction 3D image.

In one embodiment, a DRR is a synthetic x-ray image generated by casting (mathematically projecting) rays through the 3D imaging data, simulating the geometry of the in-treatment x-ray imaging system. The resulting DRR then has the same scale and pose as the treatment room x-ray imaging system, and can be compared with images from the treatment room x-ray imaging system to determine the location of the patient, or the location of the treatment target within the patient relevant to the treatment planning image reference frame. To generate a DRR, the 3D imaging data is divided into voxels (volume elements) and each voxel is assigned an attenuation (loss) value derived from the 3D imaging data. The relative intensity of each pixel in a DRR is then the summation of the voxel losses for each ray projected through the 3D image.

In one embodiment, a CBCT image (e.g., motion image 204) is taken at the beginning of a treatment delivery fraction to perform global patient alignment (translation and rotation) between the treatment planning image (e.g., 202) and the CBCT (e.g., 204). Subsequent 2D x-ray images (e.g., 208) may be registered to the planning image (202) and used to track translational changes in target position, while maintaining global rotational patient alignment achieved by the planning image (202) to CBCT (204) registration 206. 3D global patient alignment enabled by intrafraction 3D imaging may provide a higher degree of user confidence and is likely to be more flexible and reliable than existing solutions.

Figure 3A:
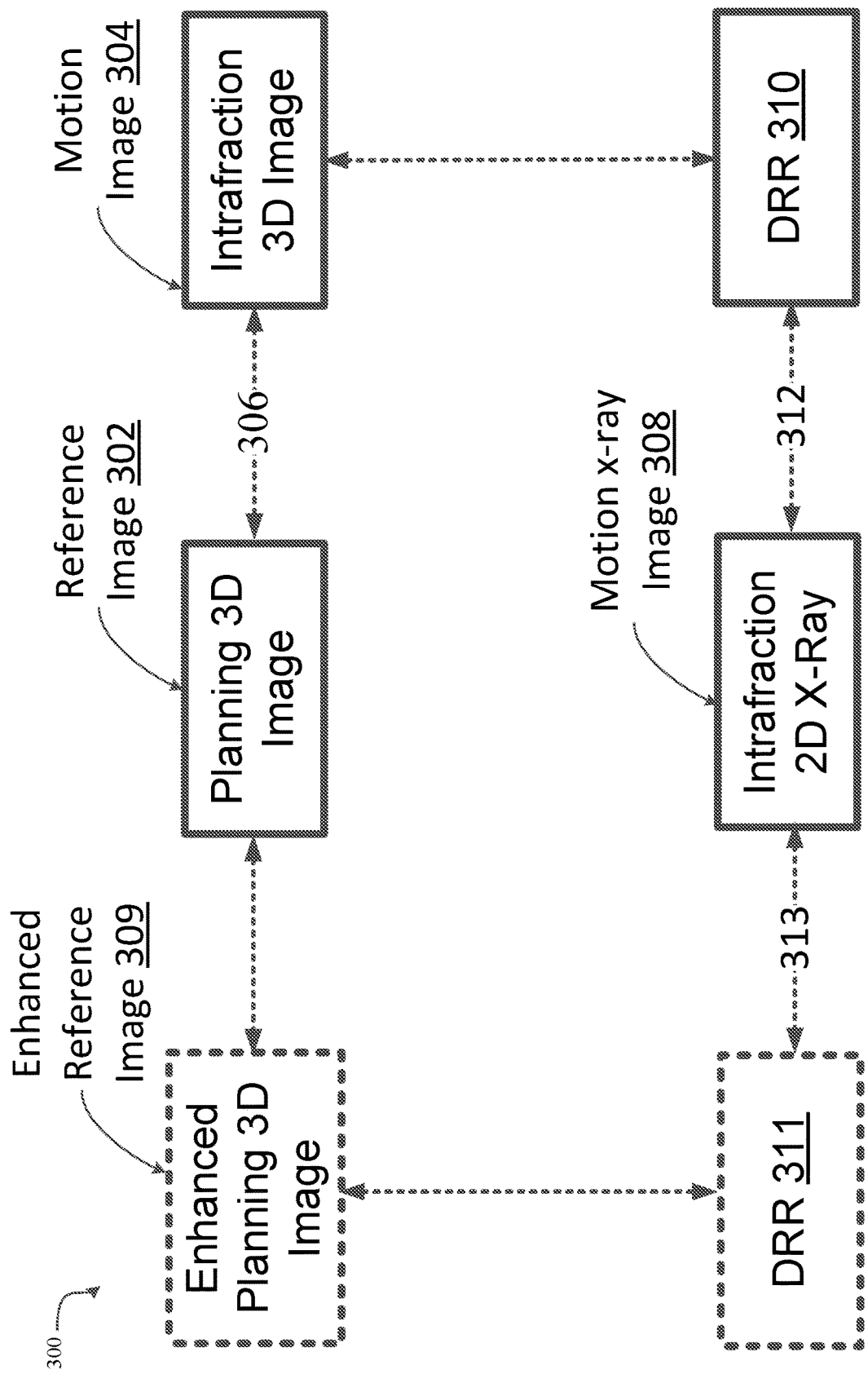
FIG. 3A illustrates an image registration pipeline in accordance with a second embodiment described herein.

FIG. 3A illustrates an image registration pipeline 300 in accordance with a second embodiment described herein. In the embodiment illustrated in FIG. 3A, a reference image 302 (e.g., a planning image) is registered to a motion image 304 (e.g., an intrafraction image) to achieve global patient alignment between plan and daily patient position. In one embodiment, the registration 306 is a three-dimensional (3D) to 3D image registration employing either 3D rigid (e.g., translation only), six-dimensional (6D) rigid (e.g., translation and rotation), or nonrigid transformation. It should be noted that these are non-limiting examples of various types of transformations that may be used, and that in alternative embodiments other transformations may be used. For example a four-dimensional (4D) transformation that is 3D rigid (translation) plus a rotation angle (roll).

In the second registration stage, a DRR 310 is generated from the Intrafraction 3D Image (304) and a 2D/3D image registration 312 is performed between intrafraction 3D image (304) and intrafraction 2D x-ray image (310) via the DRR 310. The generation of the DRR 310 from the intrafraction 3D image (304) may result in a variety of benefits. One such example is that the spatial resolution of an intrafraction CBCT image may be very high compared to a typical treatment planning CT scan (especially in the inferior superior direction). High resolution DRRs may improve accuracy and reliability of tracking algorithms, most notably the fiducial and skeletal tracking modes. Alternatively, other tracking techniques may be used. Another benefit may be that DRRs generated from intrafraction CBCT scans may reflect the daily patient pose and deformation, resulting in improved tracking. For example, a rib cage appearance may vary due to slight daily immobilization differences. Spine posture is another example of a daily patient variation.

In one embodiment, an enhanced (e.g., deformed) reference image 309 may be generated from reference image 302. Enhanced reference image 309 may be generated by combining various characteristics (e.g., one or more) of the reference image 302 and the motion image 304 in a concept referred to herein as deformable image registration (DIR). In DIR, the transformation between images is assumed to be elastic, enabling alignment of anatomical differences that result from factors such as daily variation, patient position, immobilization, and respiratory phase. A DRR 311 may be generated from the enhanced reference image 309 and a 2D/3D image registration 313 may be performed between the enhanced reference image 309 and the motion x-ray image 308. Consequently, the motion x-ray image 308 becomes implicitly registered to the motion image 304. Additional details describing DIR and the enhanced reference image 309 are described with respect to FIG. 3B.

The shape or appearance of the tracking target may change over the course of treatment (e.g., as a response to therapy). Lung target DRRs generated from an intrafraction image may provide a better appearance match (e.g., than a planning image) after two or three SBRT fractions. In another embodiment, a fiducial arrangement may change between the time a planning CT was taken and the time the patient is treated. Such fiducial migration could impact accuracy of delivering the treatment plan. An intrafraction 3D image and DRRs generated from such an image can be used to detect fiducial migration and modify the tracking algorithm to account for the changes in fiducial constellation.

In one implementation, a CBCT image (e.g., motion image 304) is taken at the beginning of a treatment fraction to perform global patient alignment. The CBCT image is registered to the treatment planning image (e.g., reference image 302) to achieve translation and rotational patient alignment. Subsequent 2D x-ray images (e.g., motion x-ray image 308) are registered to the CBCT to achieve "relative" tracking with respect to the CBCT alignment. The 2D x-ray tracking may involve both translational and rotational corrections. The registration between 2D x-ray images and the planning images is achieved implicitly due to the fact that planning 3D image and intrafraction 3D image are already registered.

Figure 3B:
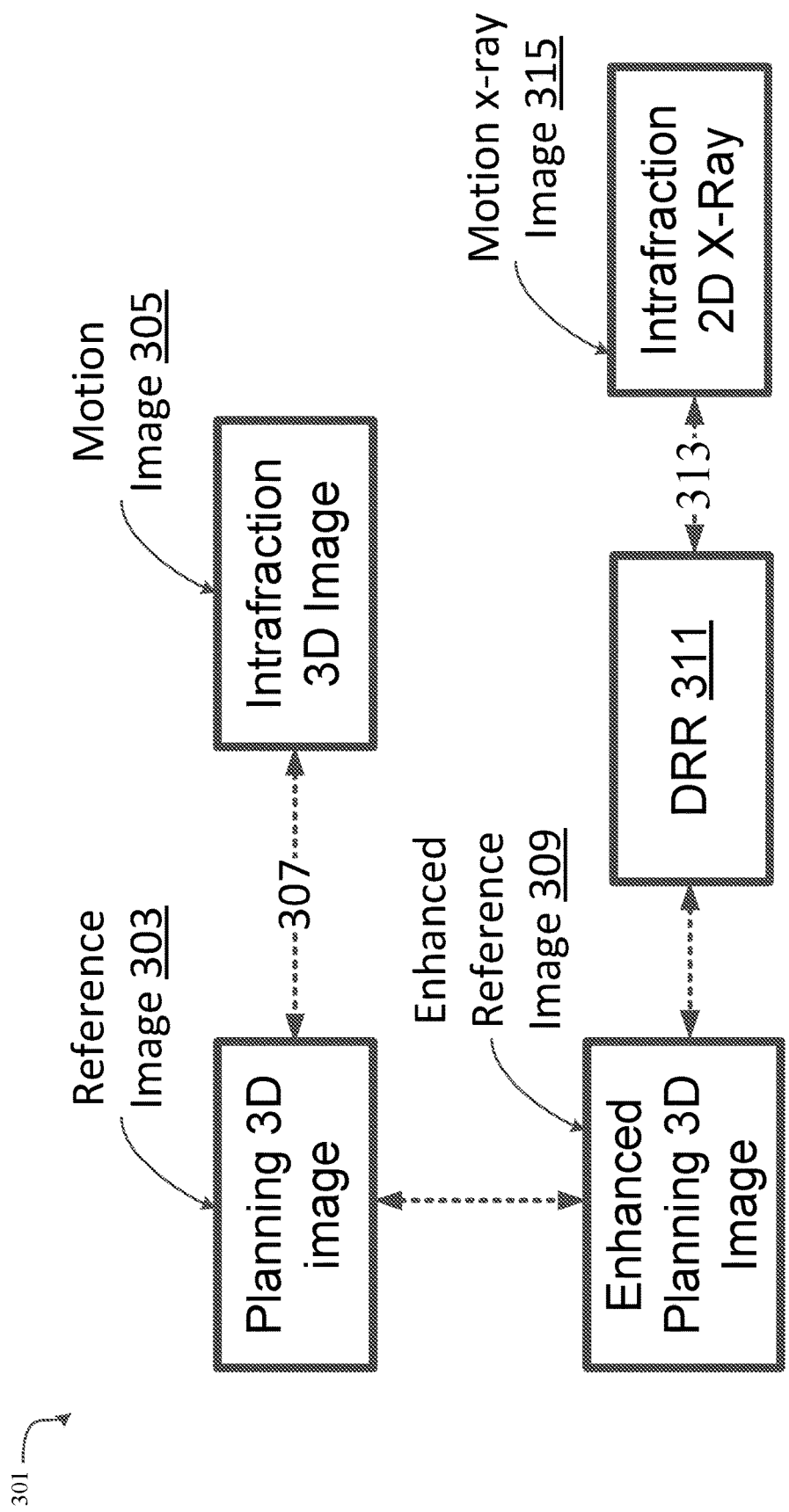
FIG. 3B illustrates an image registration pipeline in accordance with a third embodiment described herein.

FIG. 3B illustrates an image registration pipeline 301 in accordance with a third embodiment described herein. In the embodiment illustrated in FIG. 3B, a reference image 303 (e.g., a planning image) is registered to a motion image 305 (e.g., an intrafraction image) to achieve global patient alignment between plan and daily patient position. In one embodiment, the registration 307 is a three-dimensional (3D) to 3D image registration employing either 3D rigid (e.g., translation only), six-dimensional (6D) rigid (e.g., translation and rotation), or nonrigid transformation. It should be noted that these are non-limiting examples of various types of transformations that may be used, and that in alternative embodiments other transformations may be used. For example a four-dimensional (4D) transformation that is 3D rigid (translation) plus a rotation angle (roll).

In a second stage, an enhanced (e.g., deformed) reference image 309 may be generated from reference image 303. Enhanced reference image 309 may be generated by combining various characteristics of the reference image 303 and the motion image 305 in a concept referred to herein as deformable image registration (DIR). In DIR, the transformation between images is assumed to be elastic, enabling alignment of anatomical differences that result from factors such as daily variation, patient position, immobilization, and respiratory phase.

In one embodiment, a DIR algorithm uses a nonparametric non-rigid transformation to represent the deformation field. It assumes no specific parameterization of the transformation; instead it explicitly estimates the deformation field subject to smoothness regularization. Such an approach allows estimating even complex organ deformations. One DIR example optimizes the similarity criterion, local Normalized Correlation Coefficient (NCC), where Iref is the reference image neighborhood patch and Imov is the "moving" image neighborhood patch. Iref and Imov are the mean values of the volume patch.

$$NCC(I_{ref}, I_{mov}) = \frac{\Sigma_{x,y,z}(I_{ref}(x, y, z) - \bar{I}_{ref})(I_{mov}(x, y, z) - \bar{I}_{mov})}{\sqrt{\Sigma_{x,y,z}(I_{ref}(x, y, z) - \bar{I}_{ref})^2} \sqrt{\Sigma_{x,y,z}(I_{mov}(x, y, z) - \bar{I}_{mov})^2}}$$

The similarity criterion may be defined over small neighborhood patches, which may allow for robust image matching even in the presence of intensity inhomogeneities and artifacts. The image similarity criterion may be optimized iteratively over the entire image domain in a multi-resolution, coarse-to-fine scheme. The estimated deformation field may be regularized using a smoothing operator at each iteration. In one embodiment, an application uses 3 to 4 resolution levels and up to 500 iterations at each level. Worth noting is that although one DIR algorithm is described here for the purpose of clarity, any other DIR algorithm may be utilized by the embodiments described herein.

In one embodiment, a DRR 311 is generated from the enhanced reference image 309 and a 2D/3D image registration 313 is performed between the enhanced reference image 309 and the motion x-ray image 315. Consequently, the motion x-ray image 315 becomes implicitly registered to the motion image 305.

Figure 4:
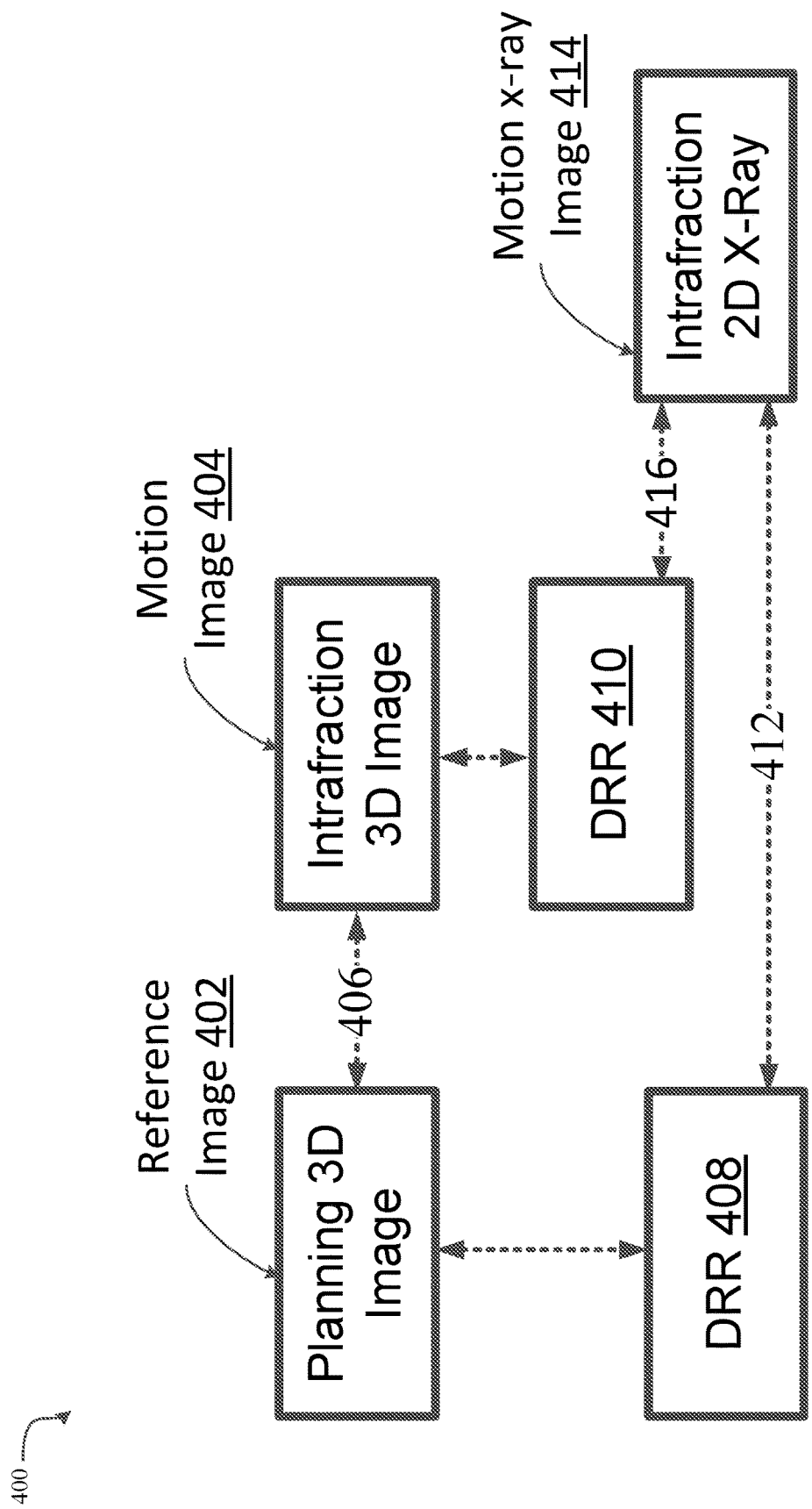
FIG. 4 illustrates an image registration pipeline in accordance with a fourth embodiment described herein.

FIG. 4 illustrates an image registration pipeline 400 in accordance with a fourth embodiment described herein. In the embodiment illustrated in FIG. 4, a reference image 402 (e.g., a planning image) is registered to a motion image 404 (e.g., an intrafraction image) to achieve global patient alignment between plan and daily patient position. In one embodiment, the registration 406 is a three-dimensional (3D) to 3D image registration employing either 3D rigid (e.g., translation only), six-dimensional (6D) rigid (e.g., translation and rotation), or nonrigid transformation. It should be noted that these are non-limiting examples of various types of transformations that may be used, and that in alternative embodiments other transformations may be used. For example a four-dimensional (4D) transformation that is 3D rigid (translation) plus a rotation angle (roll).

In one embodiment, in a second registration stage, a first DDR 408 may be generated for reference image 402, and a second DRR 410 may be generated for motion image 404. A first 2D/3D registration 412 may be performed between the intrafraction x-ray image (e.g., motion x-ray image 414) and the planning image (e.g., reference image 402) and a second 2D/3D registration 416 may be performed between the intrafraction x-ray image (e.g., motion x-ray image 414) and the intrafraction image (e.g., motion image 404). Registration to both 3D imaging modalities may provide an additional level of registration confidence (e.g., tracking confidence and quality assurance).

One example of quality assurance that may be performed more accurately is a check for fiducial migration. In case the where a fiducial migrated between the day of planning CT acquisition and the day of treatment, simultaneous (e.g., concurrent) tracking using DRRs from both the planning CT and the intrafraction 3D image may reveal a fiducial discrepancy due to fiducial migration. The check for fiducial migration may also be applied to the embodiments described with respect to FIGS. 2, 3A, and 3B.

In one embodiment, a CBCT image (e.g., motion image 404) is taken at the beginning of a treatment fraction to perform global patient alignment. The CBCT image (404) is registered to the planning image (e.g., reference image 402) to achieve translation and rotational patient alignment. Subsequent 2D x-ray images (e.g., motion x-ray image 414) are registered to DRRs (410) generated from the CBCT (404) to achieve "relative" tracking (translational and rotational) with respect to the CBCT alignment. Additionally, the 2D x-ray images (414) may be registered (translation and rotation) to DRRs (408) generated from the planning image (402) as a means of tracking quality assurance.

In a second embodiment, a CBCT image (404) is taken at the beginning of a treatment fraction to perform global patient alignment. The CBCT image (404) is registered to the planning image (402) to achieve translation and rotational patient alignment. Subsequent 2D x-ray images (414) are registered (translation and rotation) to DRRs (408) generated from the planning CT (402). Additionally, the 2D x-ray images (414) are registered (translation and rotation) to DRRs (410) generated from the CBCT image (404) as a means of tracking quality assurance. It should be noted that the operations and systems described herein may automatically (e.g., without human intervention) determine which of the types of image registration described herein may be most suitable in a given context and automatically apply the chosen registration. A suitable registration may be chosen based on any number of factors, including, but not limited to: image resolution; image clarity; target, non-target, or fiducial visibility; speed of processing; etc.

Figure 5:
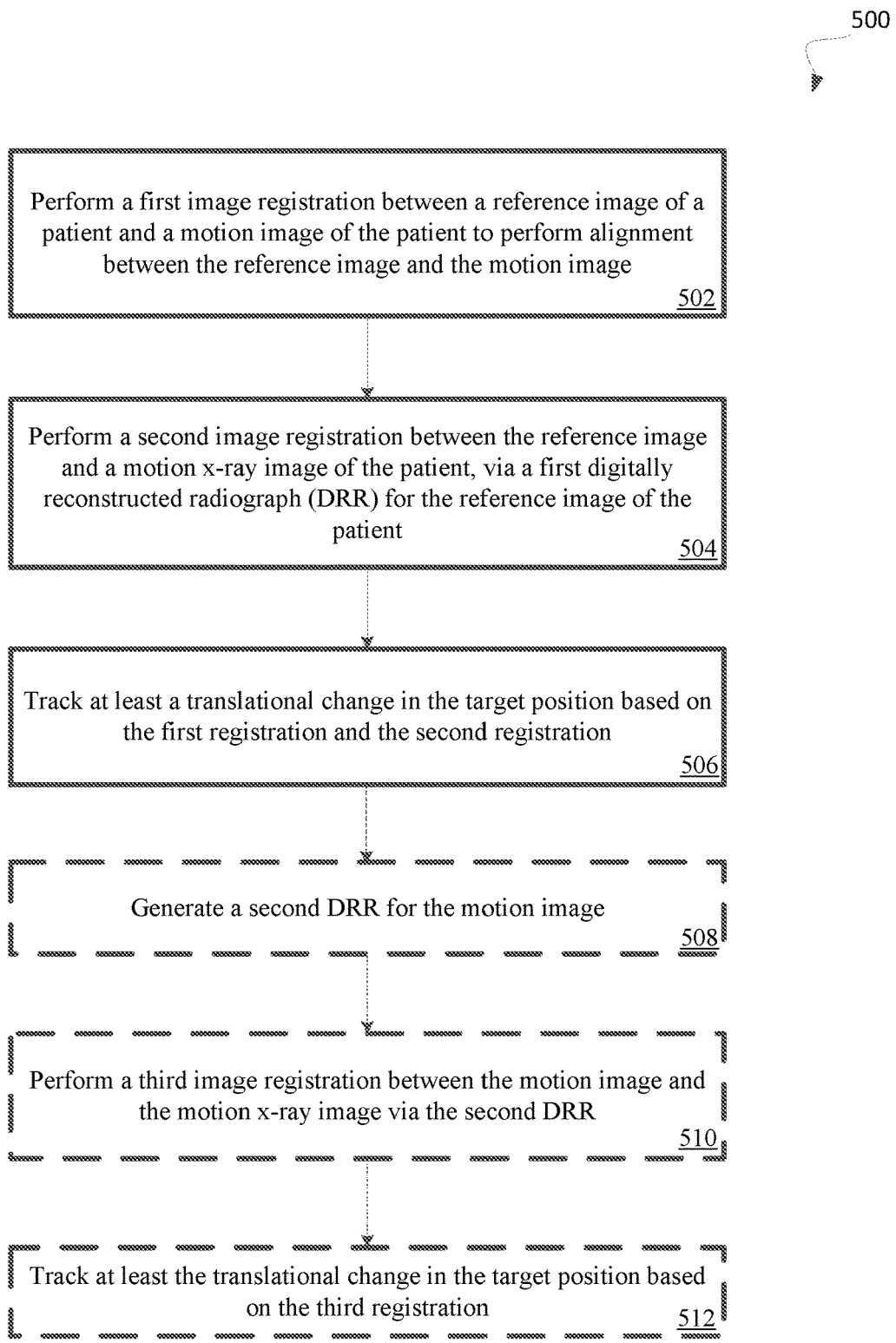
FIG. 5 illustrates a method of image registration in accordance with embodiments described herein.

FIG. 5 is a flowchart of an example method 500 of image registration in accordance with an embodiment described herein. In general, the method 500 may be performed by processing logic that may include hardware (e.g., processing device, circuitry, dedicated logic, programmable logic, microcode, hardware of a device, etc.), software (e.g., instructions run or executed on a processing device), or a combination thereof. In some embodiments, the method 500 may be performed by processing logic of the radiation treatment system 1200 of FIG. 1.

As shown in FIG. 5, the method 500 may begin with the processing logic performing a first image registration between a reference image of a patient and a motion image of the patient at block 502. In one embodiment, the reference image and the motion image include a target position of the patient. In one embodiment, the first image registration may be to perform alignment between the reference image and the motion image. In one embodiment, the reference image and the motion image are three-dimensional (3D) images. In another embodiment, the reference image is a 3D planning image that is one of a kilovoltage computed tomography (kV-CT) image, a magnetic resonance imaging (MRI) image, a kilovoltage cone beam computed tomography (kV-CBCT) image, or a megavoltage computed tomography (MVCT) image, or any other type of image. The motion image may be one of a kilovoltage cone beam computed tomography (kV-CBCT) image, a megavoltage cone beam computed tomography (MV-CBCT) image, or a megavoltage computed tomography (MVCT) image, or any other type of image.

At block 504, processing logic performs a second image registration between the reference image and a motion x-ray image of the patient, via a first digitally reconstructed radiograph (DRR) for the reference image of the patient. In one embodiment processing logic may perform the second registration to track translational changes in the target position of the patient. The motion x-ray image may be a stereo x-ray pair image, a rotating monoscopic two-dimensional (2D) x-ray image, a C-arm intraoperative image, or any other type of image.

Processing logic at block 506 may track at least the translational change in the target position based on the first registration and the second registration. In one embodiment, the reference image, the motion image, and the motion x-ray image are generated by an imaging source of a helical radiation delivery system or by one or more imaging sources at different positions with respect to the patient, as described herein. In one embodiment, processing flow may end at block 506. In another embodiment, processing flow may continue to block 508. It should be noted that blocks 508-512, as well as all other processing steps described herein, may be performed in various orders, which may vary from the orders described herein.

Continuing to block 508, processing logic may generate a second DRR for the motion image, perform a third image registration between the motion image and the motion x-ray image via the second DRR (at block 510), and track at least the translational change in the target position based on the third registration (block 512). In another embodiment, processing logic may adjust a position of the patient during an initial patient alignment, prior to initiating treatment delivery, based on the first registration and the second registration. In another embodiment, processing logic may modify a treatment delivery associated with the patient based on the first registration and the second registration.

It should be noted that the embodiments described herein can be used with various types of planning image types, including diagnostic kV-CT, MRI, kV-CBCT, and MVCT. The methods discussed herein may be used with MR-based planning (e.g., in the case where no CT is used or available for treatment planning). The embodiments discussed herein can also be used with various types of intrafraction 3D images, including kV-CBCT, MVCT, MVCBCT, and in-room helical/diagnostic kV-CT. The embodiments discussed herein can be used with various types of intrafraction 2D imaging systems, including stereo x-ray pair, a rotating monoscopic 2D x-ray imager, and C-arm intraoperative imaging systems (used in surgical and interventional guidance applications). Although the embodiments are described at times in relation to a robotic surgery system, in alternative embodiments, the method discussed herein may be used with other types of treatment delivery systems such as a helical delivery system and gantry-based systems. In addition, although the embodiments are described at times in relation to the medPhoton ImagingRing System (IRS), in alternative embodiments, the methods may be used with other types of volumetric imaging systems.

Figure 6:
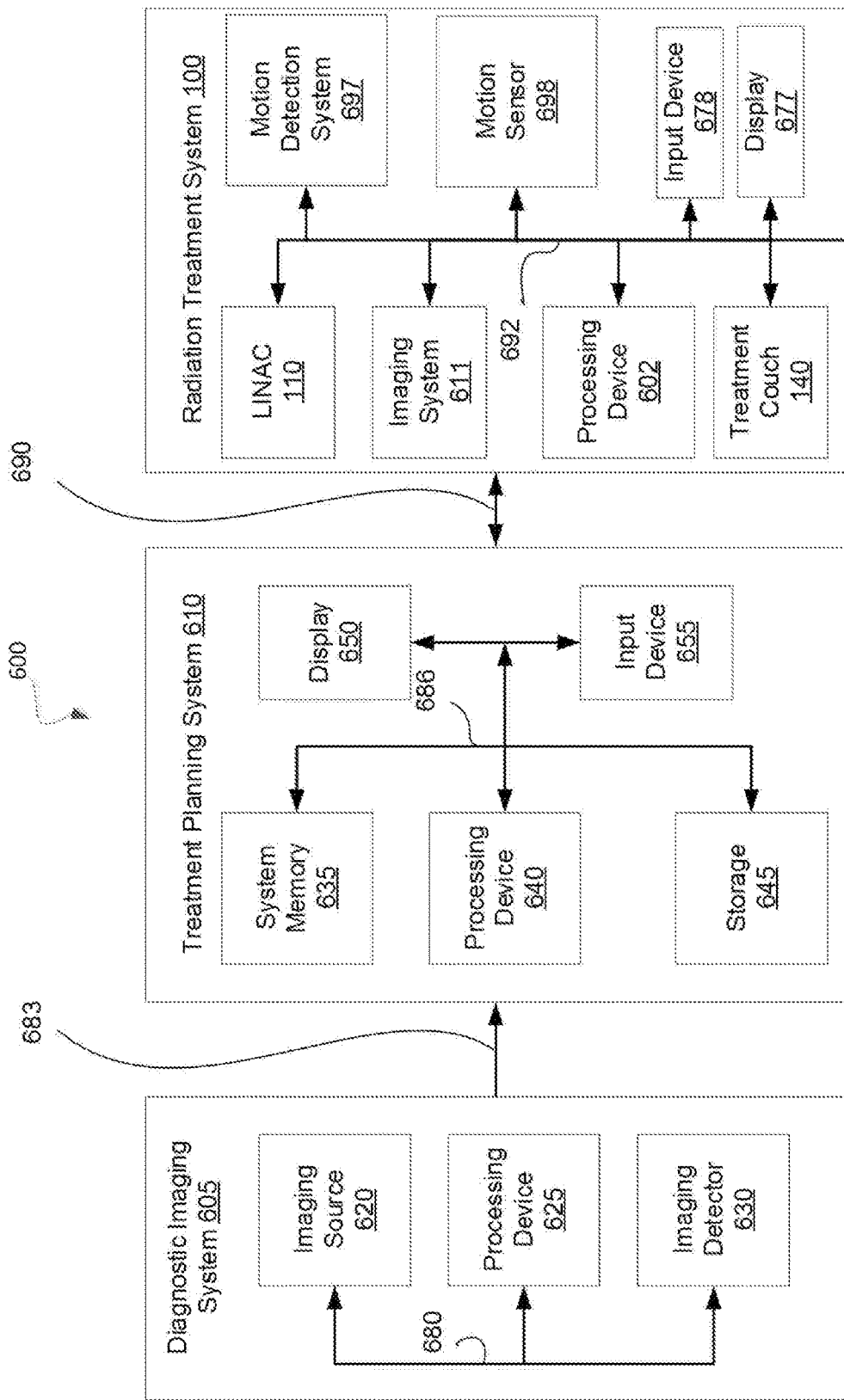
FIG. 6 illustrates a system that may be used in the generating of the performing of radiation treatment in accordance with embodiments described herein.

FIG. 6 illustrates an example machine of a computer system 600 within which a set of instructions, for causing the machine to perform any one or more of the methodologies discussed herein, may be executed. In alternative implementations, the machine may be connected (e.g., networked) to other machines in a LAN, an intranet, an extranet, and/or the Internet. The machine may operate in the capacity of a server or a client machine in client-server network environment, as a peer machine in a peer-to-peer (or distributed) network environment, or as a server or a client machine in a cloud computing infrastructure or environment.

The machine may be a personal computer (PC), a tablet PC, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The example computer system 600 includes a processing device 602, a main memory 604 (e.g., read-only memory (ROM), flash memory, dynamic random access memory (DRAM) such as synchronous DRAM (SDRAM) or Rambus DRAM (RDRAM), etc.), a static memory 606 (e.g., flash memory, static random access memory (SRAM), etc.), and a data storage device 618, which communicate with each other via a bus 630.

Processing device 602 represents one or more general-purpose processing devices such as a microprocessor, a central processing unit, or the like. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. Processing device 602 may also be one or more special-purpose processing devices such as an application specific integrated circuit (ASIC), a field programmable gate array (FPGA), a digital signal processor (DSP), network processor, or the like. The processing device 602 is configured to execute instructions 626 for performing the operations and steps discussed herein.

The computer system 600 may further include a network interface device 608 to communicate over the network 620. The computer system 600 also may include a video display unit 610 (e.g., a liquid crystal display (LCD) or a cathode ray tube (CRT)), an alphanumeric input device 612 (e.g., a keyboard), a cursor control device 614 (e.g., a mouse), a graphics processing unit 622, a signal generation device 616 (e.g., a speaker), graphics processing unit 622, video processing unit 628, and audio processing unit 632.

The data storage device 618 may include a machine-readable storage medium 624 (also known as a computer-readable medium) on which is stored one or more sets of instructions or software 626 embodying any one or more of the methodologies or functions described herein. The instructions 626 may also reside, completely or at least partially, within the main memory 604 and/or within the processing device 602 during execution thereof by the computer system 600, the main memory 604 and the processing device 602 also constituting machine-readable storage media.

In one implementation, the instructions 626 include an x-ray motion component 699 to implement functionality corresponding to the disclosure herein. While the machine-readable storage medium 624 is shown in an example implementation to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media and magnetic media.

Figure 7:
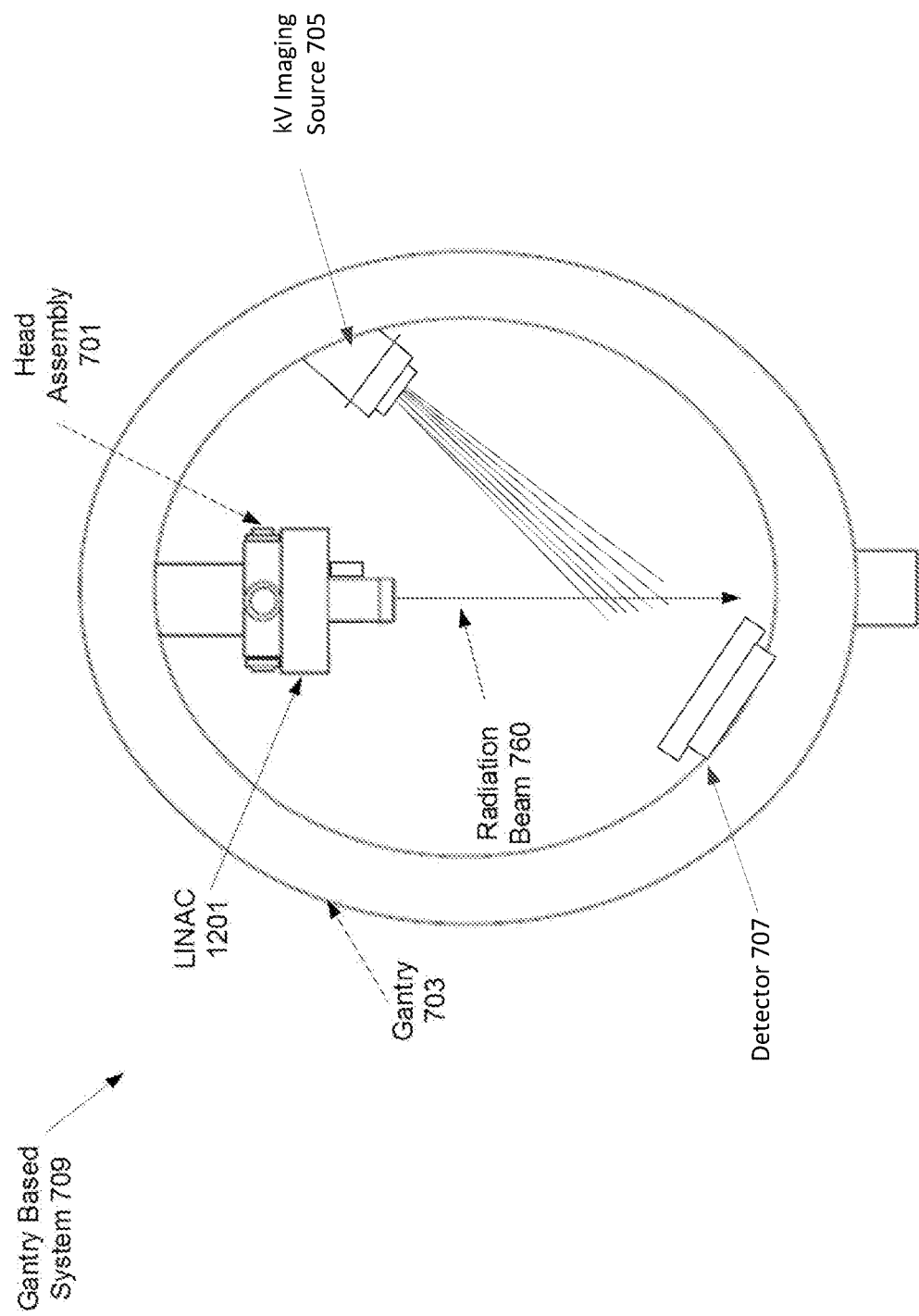
FIG. 7 illustrates a gantry based intensity modulated radiotherapy system in accordance with embodiments described herein.

FIG. 7 illustrates a gantry based intensity modulated radiotherapy (IMRT) system 709, in accordance with implementations of the present disclosure. In gantry based system 709, a radiation source (e.g., a LINAC 1201) having a head assembly 701 is mounted on a gantry 703. In one embodiment, radiation beams 160 may be delivered from several positions on a circular plane of rotation (e.g., around an axis of rotation). In one embodiment, system 709 includes a treatment imaging system, which may include a kV imaging source 705 and an x-ray detector 707. The kV imaging source 705 may be used to generate x-ray images of a ROI of patient by directing a sequence of x-ray beams at the ROI which are incident on the x-ray detector 707 opposite the kV imaging source 705 to image the patient for setup and generate in-treatment images. The resulting system generates arbitrarily shaped radiation beams 760 that intersect each other at an isocenter to deliver a dose distribution to the target location. In one implementation, the gantry based system 700 may be a c-arm based system.

Figure 8:
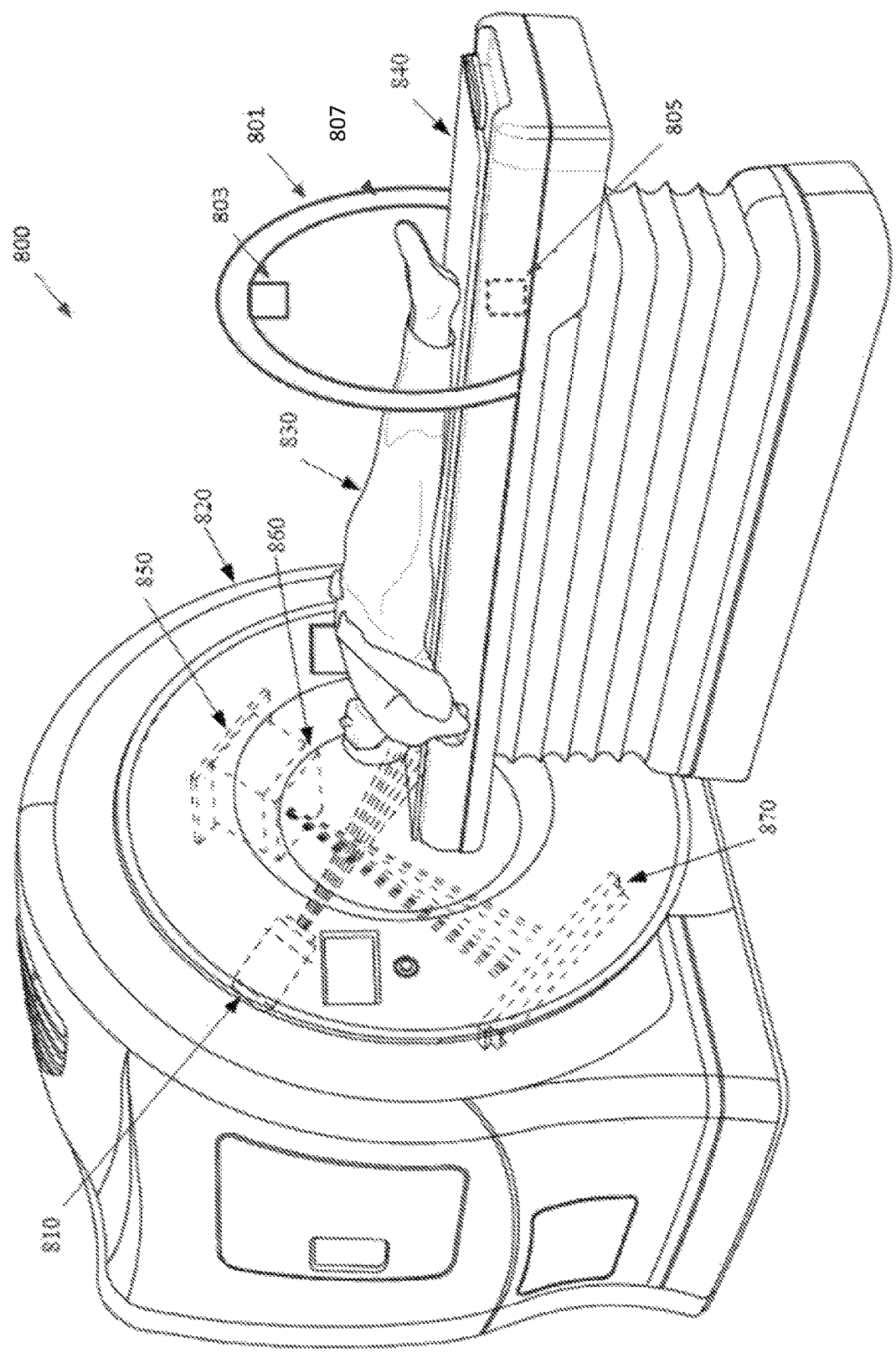
FIG. 8 illustrates a helical radiation delivery system in accordance with embodiments described herein.

FIG. 8 illustrates a helical radiation delivery system 800 in accordance with embodiments of the present disclosure. The helical radiation delivery system 800 may include a linear accelerator (LINAC) 810 mounted to a ring gantry 820. The LINAC 810 may be used to generate a narrow intensity modulated pencil beam (i.e., treatment beam) by directing an electron beam towards an x-ray emitting target. The treatment beam may deliver radiation to a target region (i.e., a tumor). The ring gantry 820 generally has a toroidal shape in which the patient 830 extends through a bore of the ring/toroid and the LINAC 810 is mounted on the perimeter of the ring and rotates about the axis passing through the center to irradiate a target region with beams delivered from one or more angles around the patient. During treatment, the patient 830 may be simultaneously moved through the bore of the gantry on treatment couch 840.

The helical radiation delivery system 800 includes a treatment imaging system, which may include a kV imaging source 850 and an x-ray detector 870. The kV imaging source 850 may be used to generate x-ray images of a region of interest (ROI) of patient 830 by directing a sequence of x-ray beams at the ROI which are incident on the x-ray detector 870 opposite the kV imaging source 850 to image the patient 830 for setup and generate in-treatment images. The treatment imaging system may further include a collimator 860. In one embodiment, the collimator 860 may be a variable aperture collimator. In another embodiment, the collimator 860 may be a multi-leaf collimator (MLC). The MLC includes a housing that houses multiple leaves that are movable to adjust an aperture of the MLC to enable shaping of an imaging x-ray beam. In another embodiment, the variable aperture collimator 860 may be an iris collimator containing trapezoidal blocks that move along a frame in a manner similar to a camera iris to produce an aperture of variable size that enables shaping of the imaging x-ray beam. The kV imaging source 850 and the x-ray detector 870 may be mounted orthogonally relative to the LINAC 810 (e.g., separated by 90 degrees) on the ring gantry 820 and may be aligned to project an imaging x-ray beam at a target region and to illuminate an imaging plane of detector 870 after passing through the patient 130. In some embodiments, the LINAC 810 and/or the kV imaging source 850 may be mounted to a C-arm gantry in a cantilever-like manner, which rotates the LINAC 810 and kV imaging source 850 about the axis passing through the isocenter. Aspects of the present disclosure may further be used in other such systems such as a gantry-based LINAC system, static imaging systems associated with radiation therapy and radiosurgery, proton therapy systems using an integrated image guidance, interventional radiology and intraoperative x-ray imaging systems, etc.

Helical radiation delivery system 800 includes also includes a secondary imaging system 801. Imaging system 801 is a CBCT imaging system, for example, the medPhoton ImagingRing System. Alternatively, other types of volumetric imaging systems may be used. The secondary imaging system 801 includes a rotatable gantry 807 (e.g., a ring) attached to anarm and rail system (not shown) that move the rotatable gantry 807 along one or more axes (e.g., along an axis that extends from a head to a foot of the treatment couch 840. An imaging source 803 and a detector 805 are mounted to the rotatable gantry 807. The rotatable gantry 807 may rotate 360 degrees about the axis that extends from the head to the foot of the treatment couch. Accordingly, the imaging source 803 and detector 805 may be positioned at numerous different angles. In one embodiment, the imaging source 803 is an x-ray source and the detector 805 is an x-ray detector. In one embodiment, the secondary imaging system 801 includes two rings that are separately rotatable. The imaging source 803 may be mounted to a first ring and the detector 805 may be mounted to a second ring.

It will be apparent from the foregoing description that aspects of the present disclosure may be embodied, at least in part, in software. That is, the techniques may be carried out in a computer system or other data processing system in response to a processing device 625, 640, or 602 (see FIG. 6), for example, executing sequences of instructions contained in a memory. In various implementations, hardware circuitry may be used in combination with software instructions to implement the present disclosure. Thus, the techniques are not limited to any specific combination of hardware circuitry and software or to any particular source for the instructions executed by the data processing system. In addition, throughout this description, various functions and operations may be described as being performed by or caused by software code to simplify description. However, those skilled in the art will recognize what is meant by such expressions is that the functions result from execution of the code by processing device 625, 640, or 602.

A machine-readable medium can be used to store software and data which when executed by a general purpose or special purpose data processing system causes the system to perform various methods of the present disclosure. This executable software and data may be stored in various places including, for example, system memory and storage or any other device that is capable of storing at least one of software programs or data. Thus, a machine-readable medium includes any mechanism that provides (i.e., stores) information in a form accessible by a machine (e.g., a computer, network device, personal digital assistant, manufacturing tool, any device with a set of one or more processors, etc.). For example, a machine-readable medium includes recordable/non-recordable media such as read only memory (ROM), random access memory (RAM), magnetic disk storage media, optical storage media, flash memory devices, etc. The machine-readable medium may be a non-transitory computer readable storage medium.

Unless stated otherwise as apparent from the foregoing discussion, it will be appreciated that terms such as "receiving," "positioning," "performing," "emitting," "causing," or the like may refer to the actions and processes of a computer system, or similar electronic computing device, that manipulates and transforms data represented as physical (e.g., electronic) quantities within the computer system's registers and memories into other data similarly represented as physical within the computer system memories or registers or other such information storage or display devices. Implementations of the methods described herein may be implemented using computer software. If written in a programming language conforming to a recognized standard, sequences of instructions designed to implement the methods can be compiled for execution on a variety of hardware platforms and for interface to a variety of operating systems. In addition, implementations of the present disclosure are not described with reference to any particular programming language. It will be appreciated that a variety of programming languages may be used to implement implementations of the present disclosure.

It should be noted that the methods and apparatus described herein are not limited to use only with medical diagnostic imaging and treatment. In alternative implementations, the methods and apparatus herein may be used in applications outside of the medical technology field, such as industrial imaging and non-destructive testing of materials. In such applications, for example, "treatment" may refer generally to the effectuation of an operation controlled by the treatment planning system, such as the application of a beam (e.g., radiation, acoustic, etc.) and "target" may refer to a non-anatomical object or area.

In the foregoing specification, the disclosure has been described with reference to specific exemplary implementations thereof. It will, however, be evident that various modifications and changes may be made thereto without departing from the broader spirit and scope of the disclosure as set forth in the appended claims. The specification and drawings are, accordingly, to be regarded in an illustrative sense rather than a restrictive sense.

What is claimed is:

1. A method, comprising:
performing, by a processing device, a first image registration between a reference image of a patient and a motion image of the patient to perform alignment between the reference image and the motion image, wherein the reference image and the motion image include a target position of the patient;
performing, by the processing device, a second image registration between the reference image and a motion x-ray image of the patient, via a first digitally reconstructed radiograph (DRR) for the reference image of the patient; and
tracking at least a translational change in the target position based on the first registration anc the second registration.

2. The method of claim 1, wherein the reference image and the motion image are three-dimensional (3D) images.

3. The method of claim 2, wherein the reference image is a 3D planning image.

4. The method of claim 2, wherein the reference image is one of: a kilovoltage computed tomography (kV-CT) image, a magnetic resonance imaging (MRI) image, a kilovoltage cone beam computed tomography (kV-CBCT) image, or a megavoltage computed tomography (MVCT) image.

5. The method of claim 2, wherein the motion image is one of: a kilovoltage cone beam computed tomography (kV-CBCT) image, a megavoltage cone beam computed tomography (MV-CBCT) image, a megavoltage computed tomography (MVCT) image, or a helical kV-CT image.

6. The method of claim 1, wherein the first image registration is used to perform a global rotational patient alignment, and wherein the second image registration is used to maintain the global rotational patient alignment.

7. The method of claim 1, further comprising:
generating a second DRR, wherein the second DRR is of the motion image;
performing a third image registration between the motion image and the motion x-ray image via the second DRR; and
tracking at least the translational change in the target position based on the third registration.

8. The method of claim 1, wherein the reference image, the motion image, and the motion x-ray image are generated by an imaging source of a helical radiation delivery system or by one or more imaging sources at different positions with respect to the patient.

9. The method of claim 1, further comprising:
detecting a fiducial migration associated with the patient based on the first DRR; and
modifying a tracking algorithm associated with a treatment delivery of the patient to account for the fiducial migration.

10. A system comprising:
a memory; and
a processing device, operatively coupled with the memory, to:
performing a first image registration between a reference image of a patient and a motion image of the patient to perform alignment between the reference image and the motion image, wherein the reference image and the motion image include a target position of the patient;
performing a second image registration between the reference image and a motion x-ray image of the patient, via a first digitally reconstructed radiograph (DRR) for the reference image of the patient; and
track at least a translational change in the target position based on the first registration and the second registration.

11. The system of claim 10, wherein the reference image is one of: a kilovoltage computed tomography (kV-CT) image, a magnetic resonance imaging (MRI) image, a kilovoltage cone beam computed tomography (kV-CBCT) image, or a megavoltage computed tomography (MVCT) image.

12. The system of claim 10, wherein the motion image is one of: a kilovoltage cone beam computed tomography (kV-CBCT) image, a megavoltage cone beam computed tomography (MV-CBCT) image, a megavoltage computed tomography (MVCT) image, or a helical kV-CT image.

13. A non-transitory computer readable medium comprising instructions that, when executed by a processing device, cause the processing device to:
perform, by a processing device, a first image registration between a reference image of a patient and a motion image of the patient to perform alignment between the reference image and the motion image, wherein the reference image and the motion image include a target position of the patient;
perform, by the processing device, a second image registration between the reference image and a motion x-ray image of the patient, via a first digitally reconstructed radiograph (DRR) for the reference image of the patient; and
track at least a translational change in the target position based on the first registration and the second registration.

14. The non-transitory computer readable medium of claim 13, the processing device further to:
generate a second DRR, wherein the second DRR is of the motion image;
perform a third image registration between the motion image and the motion x-ray image via the second DRR; and
track at least the translational change in the target position based on the third registration.

15. The non-transitory computer readable medium of claim 13, wherein the reference image, the motion image, and the motion x-ray image are generated by an imaging source of a helical radiation delivery system or by one or more imaging sources at different positions with respect to the patient.

16. The non-transitory computer readable medium of claim 13, the processing device further to:
    detect a fiducial migration associated with the patient based on the first DRR; and
    modify a tracking algorithm associated with a treatment delivery of the patient to account for the fiducial migration.

17. A method, comprising:
    performing, by a processing device, a first image registration between a reference image of a patient and a motion image of the patient, to perform alignment between the reference image and the motion image, wherein the reference image and the motion image include a target position of the patient;
    performing, by the processing device, a second image registration between the motion image and a motion x-ray image of the patient, via a first digitally reconstructed radiograph (DRR) for the motion image; and
    tracking at least a translational change in the target position based on the first registration and the second registration.

18. The method of claim 17, wherein the motion image has a higher spatial resolution than the reference image.

19. The method of claim 17, wherein the reference image is one of: a kilovoltage computed tomography (kV-CT) image, a magnetic resonance imaging (MRI) image, a kilovoltage cone beam computed tomography (kV-CBCT) image, or a megavoltage computed tomography (MVCT) image.

20. The method of claim 17, wherein the motion image is one of: a kilovoltage cone beam computed tomography (kV-CBCT) image, a megavoltage cone beam computed tomography (MV-CBCT) image, a megavoltage computed tomography (MVCT) image, or a helical kV-CT image.

21. The method of claim 17, wherein the first DRR corresponds to a daily patient pose and deformation.

22. The method of claim 17, further comprising:
    detecting a fiducial migration associated with the patient based on the first DRR; and
    modifying a tracking algorithm associated with a treatment delivery of the patient to account for the fiducial migration.

23. The method of claim 17, further comprising:
    performing a third image registration between an enhanced reference image and the motion x-ray image of the patient, via a second DRR, wherein the second DRR is of the enhanced reference image; and
    tracking at least the translational change in the target position based on the third registration.

24. The method of claim 23, wherein the enhanced reference image is generated by combining one or more characteristics of the reference image of the patient with one or more characteristics of the motion image.

25. A system comprising:
    a memory; and
    a processing device, operatively coupled with the memory, to:
        perform a first image registration between a reference image of a patient and a motion image of the patient, to perform alignment between the reference image and the motion image, wherein the reference image and the motion image include a target position of the patient;
        perform a second image registration between the motion image and a motion x-ray image of the patient, via a first digitally reconstructed radiograph (DRR) for the motion image; and
        track at least a translational change in the target position based on the first registration and the second registration.

26. The system of claim 25, wherein the motion image is one of: a kilovoltage cone beam computed tomography (kV-CBCT) image, a megavoltage cone beam computed tomography (MV-CBCT) image, a megavoltage computed tomography (MVCT) image, or a helical kV-CT image.

27. The system of claim 25, the processing device further to:
    detect a fiducial migration associated with the patient based on the first DRR; and
    modify a tracking algorithm associated with a treatment delivery of the patient to account for the fiducial migration.

28. A non-transitory computer readable medium comprising instructions that, when executed by a processing device, cause the processing device to:
    perform, by a processing device, a first image registration between a reference image of a patient and a motion image of the patient, to perform alignment between the reference image and the motion image, wherein the reference image and the motion image include a target position of the patient;
    perform, by the processing device, a second image registration between the motion image and a motion x-ray image of the patient, via a first digitally reconstructed radiograph (DRR) for the motion image; and
    track at least a translational change in the target position based on the first registration and the second registration.

29. The non-transitory computer readable medium of claim 28, the processing device further to:
    perform a third image registration between an enhanced reference image and the motion x-ray image of the patient, via a second DRR, wherein the second DRR is of the enhanced reference image; and
    track at least the translational change in the target position based on the third registration.

30. The non-transitory computer readable medium of claim 28, wherein the reference image, the motion image, and the motion x-ray image are generated by an imaging source of a helical radiation delivery system or by one or more imaging sources at different positions with respect to the patient.

* * * * *